United States Patent
Kawahara et al.

(10) Patent No.: US 12,178,204 B2
(45) Date of Patent: Dec. 31, 2024

(54) LOW-TEMPERATURE DAMAGE-RELIEVING AGENT OR NECROSIS INHIBITOR, AND METHOD FOR PRESERVING LIVING ORGANISM, TISSUE OR CELL

(71) Applicant: SHIN NIPPON YAKUGYO CO., LTD., Tokyo (JP)

(72) Inventors: Hidehisa Kawahara, Osaka (JP); Eri Tagawa, Osaka (JP)

(73) Assignee: SHIN NIPPON YAKUGYO CO., LTD., Tokyo (JP)

(*) Notice: Subject to any disclaimer, the term of this patent is extended or adjusted under 35 U.S.C. 154(b) by 686 days.

(21) Appl. No.: 16/636,592

(22) PCT Filed: Aug. 1, 2018

(86) PCT No.: PCT/JP2018/028923
§ 371 (c)(1),
(2) Date: Feb. 4, 2020

(87) PCT Pub. No.: WO2019/031365
PCT Pub. Date: Feb. 14, 2019

(65) Prior Publication Data
US 2020/0367487 A1 Nov. 26, 2020

(30) Foreign Application Priority Data
Aug. 8, 2017 (JP) .................................. 2017-152902

(51) Int. Cl.
*A01N 1/02* (2006.01)

(52) U.S. Cl.
CPC ......... *A01N 1/0221* (2013.01); *A01N 1/0284* (2013.01)

(58) Field of Classification Search
CPC .. A01N 1/0221; A01N 1/0284; A01N 1/0226; A23F 5/26; C12N 2511/00
See application file for complete search history.

(56) References Cited

U.S. PATENT DOCUMENTS

| | | | |
|---|---|---|---|
| 8,226,992 | B1 | 7/2012 | Okerlin, III |
| 10,392,599 | B2 | 8/2019 | Ideta et al. |
| 2017/0079462 | A1* | 3/2017 | Ait Bouziad ......... A47J 43/046 |

FOREIGN PATENT DOCUMENTS

| | | |
|---|---|---|
| CN | 102300578 A | 12/2011 |
| JP | 2001139599 A | 5/2001 |

(Continued)

OTHER PUBLICATIONS

Danielle Walker "Pumpkin Spice Latte" https://againstallgrain.com/2014/10/16/pumpkin-spice-latte/ (Year: 2014).*

(Continued)

*Primary Examiner* — Blaine Lankford
*Assistant Examiner* — Lauren K Van Buren
(74) *Attorney, Agent, or Firm* — CANTOR COLBURN LLP

(57) ABSTRACT

An organ, a tissue or cells of a living body can be preserved stably at a non-freezing low temperature without damaging the organ, the tissue or the cells, by the method of preserving an organ, a tissue or cells of a living body by using the low temperature damage alleviating agent or the necrosis inhibitor comprising a coffee extract of the present invention, or a medium comprising a coffee extract.

7 Claims, 1 Drawing Sheet

(56) References Cited

FOREIGN PATENT DOCUMENTS

| JP | 2003250572 A | 9/2003 |
|---|---|---|
| JP | 2015038170 A | 2/2015 |
| JP | 2016039792 A | 3/2016 |
| JP | 6423998 B2 | 11/2018 |
| WO | 2002001952 A1 | 1/2004 |
| WO | 2010065567 A2 | 6/2010 |
| WO | 2014030211 A1 | 2/2014 |

OTHER PUBLICATIONS

Goya et al. "Effect of coffee Melanoidin on human hepatoma HepG2 Cells. Protection against oxidative stress induced by tert-butylhydroperoxide" Mol. Nutr. Food Res. 2007, 51, 536-545. (Year: 2007).*

Goya et al. "Effect of Coffee Melanoidin on human hepatoma HepG2 cells" Protection against oxidative stress induced bytert-butylhydroperoxide Mol. Nutri. Food Res, 2007, 51, 536-545. (Year: 2007).*

Delgado-Andrade et al. "Unraveling the Contribution of Melanoidins to the Antioxidant Activity of Coffee Brews" J. Agri. Food, Chem, 2005, 53, 1403-1407. (Year: 2005).*

Zhang et al. "DAMPs and autophagy, Cellular Adaption to injury and unscheduled cell death," Autophagy, 9: 4,451-458, Apr. 2013. (Year: 2013).*

Extended European Search Report for EP Application No. 18843057. 3; Date of Mailing—Mar. 23, 2021, 8 pages.

Runti et al., "Arabica Coffee Extract Shows Antibacterial Activity Against *Staphylococcus epidermidis* and Enterococcus Faecalis and Low Toxicity toward a Human Cell Line," LWT—Food Science Technology, No. 62 (2015) pp. 108-114.

Kawahara, "Extraction of New Food Material Extracts From Coffee Grounds, and Functionality Thereof," Abstracts of Project Study Report, Innovative Technology World, (2014), (No. 138), pp. 101-102.

Kawahara, "Production of Supercooling Promoting Substances Derived From Natural Products, and Development of their Application," Lectures of 21st Kansai University Integrated Science and Technology Symposium, (2017), pp. 192-194.

Ohashi et al., "Supercooling Preservation of Egg Cells and Ovaries Using an Extract Derived from Coffee Grounds," Journal of Mammalian Ova Research, (2015), vol. 32, (No. 2), p. S16.

Wikipedia the Free Encyclopedia, "Cell Isolation Definition," Retrieved from https://en.wikipedia.org, 4 pages.

Monente et al., "Coffee and Spent Coffee Extracts Protect Against Cell Mutagens and Inhibit Growth of Food-borne Pathogen Microorganisms," Journal of Functional Foods, (2015), vol. 12, 365-374.

CN Office Action and English Translation for Application No. 201880037516.X, dated Feb. 24, 2023.

Retrieved from Website: https://en.wikipedia.org/wiki/Cell_isolation, 4 pages.

Retrieved from Website: https://www.collinsdictionary.com/dictionary/english/cell-isolation, 4 pages.

Wikipedia the Free Encyclopedia, "Freezing-point depression," Retrieved from: https://en-wikipedia.org/w/index.php?title=Freezing-point_depression&oldid-1190048846, seven pages.

Yamauchi et al., "Subzero nonfreezing hypothermia with insect antifreeze protein dramatically improves survival rate of mammalian cells," International Journal of Molecular Sciences, (2021), vol. 22, (No. 12680), 1-14.

* cited by examiner

LOW-TEMPERATURE DAMAGE-RELIEVING AGENT OR NECROSIS INHIBITOR, AND METHOD FOR PRESERVING LIVING ORGANISM, TISSUE OR CELL

CROSS REFERENCE TO RELATED APPLICATIONS

This application is a National Stage application of PCT/JP2018/028923, filed Aug. 1, 2018, which claims priority to Japanese Application No. 2017-152902, filed Aug. 8, 2017, and all the benefits accruing therefrom under 35 U.S.C. § 119, the content of which is incorporated by reference in its entirety.

TECHNICAL FIELD

The present invention relates to a low temperature damage alleviating agent or necrosis inhibitor comprising a coffee extract, and a method of preserving an organ, a tissue or cells of a living body.

BACKGROUND ART

In transplantation, reconstruction and the like of an organ, a tissue, cells or the like of a living body, the organ and the like are preserved in a fresh state, and transferred as needed until surgery. In recent years, regenerative medicine using iPS cells, stem cells or the like has attracted attention. In regenerative medicine, it is sometimes necessary to preserve an organ, a tissue, cells or the like of a living body.

For example, a rapid freezing preservation method, a vitrification freezing method, refrigeration and the like are used as a method of preserving an organ and the like of a living body. However, cell viabilities in the rapid freezing preservation method generally decrease by tissue destruction due to ice crystal formation. The vitrification freezing method is a method in which an anti-freezing agent such as glycerin exhibiting high cytotoxicity is used at a high concentration, and cells and the like are damaged by recrystallization when dissolved. When cells and the like are preserved frozen, there is also a problem that it takes a considerable time to recover the cells and the like from cryopreservation. Therefore, it is preferable to preserve cells and the like alive rather than cryopreservation.

An organ and the like of a living body are refrigerated and preserved, for example, at 0 to 4° C. Although refrigeration preservation may be easily applied, it is know that metabolism of a living body is only reduced to about ¹⁄₁₀ of normal one at 4° C., and it is reduced to about ¹⁄₁₇ of normal one at −4° C. in a non-freezing state. Therefore, it is preferable to preserve an organ and the like alive at a non-freezing low temperature rather than refrigeration preservation at 0 to 4° C., because ATP depletion during preservation can be delayed.

Patent Literature 1 discloses a method of preserving a living tissue or cells in an electric field space having a field intensity of 0.3 kV/m to 1.0 kV/m, which prepares a state to generate supercooling so that water is in a non-freezing state at a temperature below the freezing point of water. However, this method has a problem that a complicated apparatus is necessary to perform this method. Accordingly, there is a need for a simple method of preserving an organ and the like of a living body at a non-freezing low temperature which does not require a complicated apparatus.

Patent Literature 2 discloses a method of preserving a mammalian embryo(s) or fertilized egg(s), said method comprising preserving immersing the mammalian embryo(s) or fertilized egg(s) in a medium comprising 20 to 80% (v/v) serum and 10 to 100 mM Good's buffer, and storing the embryo(s) or fertilized egg(s) at a non-freezing low temperature. However, the effects of this method are still insufficient in that damages of an organ and the like of a living body occur.

The present applicant proposed in Patent Literature 3 a supercooling accelerating substance using compounds having an aromatic hydrocarbon structure and a carboxyl group extracted from coffee beans. However, it has not been known that this supercooling accelerating substance alleviates low temperature damage of an organ or the like, or inhibits necrosis at a non-freezing low temperature.

CITATION LIST

Patent Literature

Patent Literature 1: JP 2016-039792
Patent Literature 2: WO 2014/030211
Patent Literature 3: JP 2015-038170

SUMMARY OF THE INVENTION

Technical Problem

An problem to be solved by the present invention is to provide a method of preserving (or storing) an organ, a tissue or cells of a living body at a non-freezing low temperature stably without damaging the organ, the tissue or the cells; and to provide a low temperature damage alleviating agent or a necrosis inhibitor capable of being used for the method or the like.

Solution to the Problem

The present inventors have intensively studied to solve the above mentioned problems. As a result of the study, the present inventors have surprisingly found that a coffee extract alleviates low temperature damage of cells at a non-freezing low temperature, and also remarkably inhibits necrosis, and have completed the present inventions. That is, the present inventions are as follows.

[1] A low temperature damage alleviating agent or a necrosis inhibitor comprising a coffee extract.
[2] The low temperature damage alleviating agent or the necrosis inhibitor according to [1], wherein the coffee extract is a hot water extract of coffee or a coffee melanoidin.
[3] A method of preserving an organ, a tissue or cells of a living body by using a medium comprising a coffee extract.
[4] The method of preserving an organ, a tissue or cells of a living body according to [3], wherein the organ, the tissue or the cells is preserved at a non-freezing low temperature.
[5] The method of preserving an organ, a tissue or cells of a living body according to [3] or [4], wherein the coffee extract is a hot water extract of coffee or a coffee melanoidin.
[6] A method of alleviating a low temperature damage of an organ, a tissue or cells of a living body, or a method of inhibiting necrosis of an organ, a tissue or cells of a living body, by applying a coffee extract to the living organ, the tissue or the cells.

[7] The method of alleviating a low temperature damage of an organ, a tissue or cells of a living body, or the method of inhibiting necrosis of an organ, a tissue or cells of a living body according to [6], wherein the coffee extract is a hot water extract of coffee or a coffee melanoidin.

Advantageous Effects of the Invention

An organ, a tissue or cells of a living body can be preserved (or stored) at a non-freezing low temperature stably without damaging the organ, the tissue or the cells, by using the low temperature damage alleviating agent or the necrosis inhibitor of the present invention, or by the method of preserving an organ, a tissue or cells of a living body of the present invention. The present invention may be widely used for transplantation, reconstruction and the like of an organ, a tissue, cells or the like of a living body; and regenerative medicine using iPS cells, stem cells or the like; and further, an experiment or the like of an organ, a tissue or cells of a living body in research facilities.

DESCRIPTION OF THE INVENTION

1. A Coffee Extract

Figure 1:
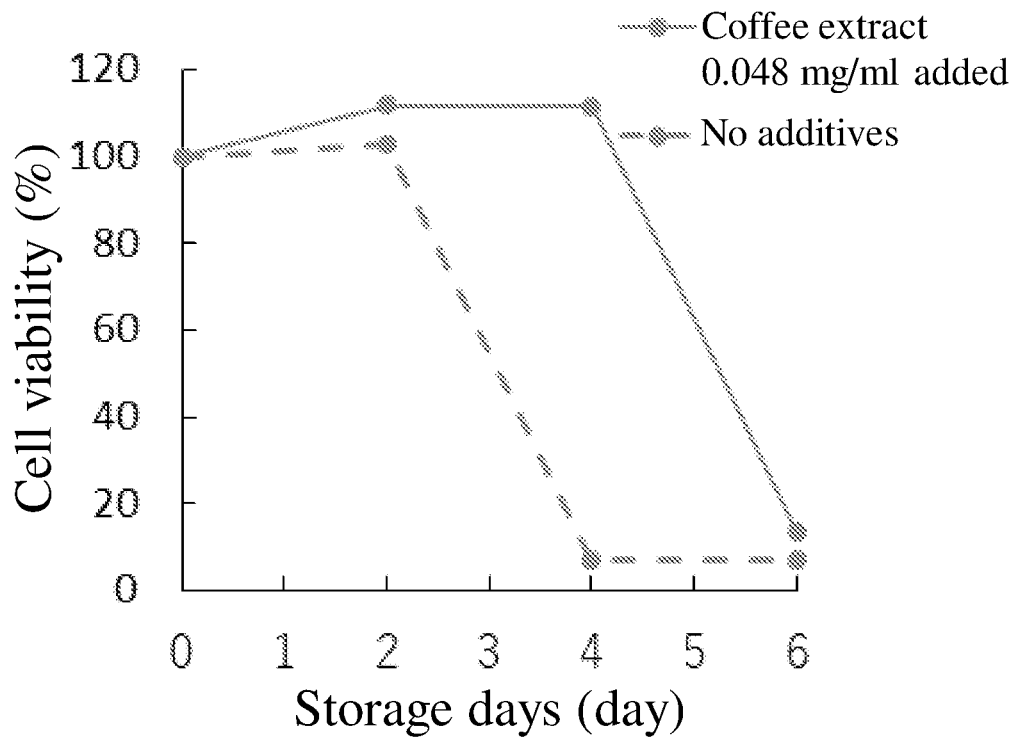
FIG. 1 shows a figure exhibiting the test result of the coffee extract in Example 1.

A coffee extract used in the present invention is one extracted from coffee beans. The coffee extract includes, for example, a coffee extract containing compounds having at least an aromatic hydrocarbon structure and a carboxyl group in the compounds (JP 2015-038170). The structure of the coffee extract and the production method thereof are as described in JP 2015-038170.

The coffee beans include beans of a plant belonging to Coffea. For example, beans of arabica (Coffea arabica) and robusta (Coffea canephora) are preferably used. The coffee beans are preferably used after roasting. A general method of roasting coffee beans may be used for roasting. Roasting may be performed by heating the coffee beans at a temperature exceeding the boiling point of water, for example, 150 to 200° C. It is preferred to crush the coffee beans prior to extraction.

Extraction is performed using water or a water containing organic solvent, preferably water, as an extraction solvent. The water containing organic solvent include one containing 90% by mass or more of water. The organic solvent in the water containing organic solvent includes an alcohol such as methanol. It is preferable to adjust pH of water or the water containing organic solvent to 6 to 8. An extraction temperature is, for example, room temperature to 120° C., preferably about 90 to 100° C. An extraction time is, for example, about 30 min to 24 hours. For example, extraction may also be performed in a pressurized state using an autoclave or the like. An amount of the extraction solvent may be, for example, 1 to 5 parts by volume with respect to 1 part by mass of the dried coffee beans. The extract liquid is further subjected to an operation such as filtration, precipitation, centrifugation, and drying as needed.

The coffee extract used in the present invention can be obtained by the above operation. Moreover, commercial instant coffee powders and a commercial coffee drink may also be used as the coffee extract. As needed, the coffee extract may be subjected to a fractionation step of performing a fractionation treatment according to a molecular weight; a pH adjustment step of adjusting the pH; an organic solvent extraction step of performing an extraction treatment with an organic solvent; a purification step of performing a purification treatment; or the like.

In the fractionation step, fractionation is performed according to a molecular weight by a general fractionation treatment method. A fractionation treatment method by a dialysis membrane capable of fractionation according to a predetermined molecular weight, a fractionation treatment method by an ion exchange chromatography, a fractionation treatment method by an ultrafiltration membrane, or the like, may be adopted as a fractionation treatment method. In the fractionation step, a liquid for fractionation treatment is prepared, for example, by dilution of the coffee extract with water, or the like. Using an ultrafiltration membrane whose fractional molecular weight is set to a predetermined value, components exceeding the predetermined molecular weight and components having the predetermined molecular weight or less are obtained. For example, components contained in the water extract obtained by the water extraction step are fractionated into components having a molecular weight exceeding 10,000 and components having a molecular weight of 10,000 or less.

In the pH adjustment step, pH of the fractionated fraction liquid is adjusted by a general method. In the pH adjustment step, for example, pH of the fractionated fraction liquid containing components having a molecular weight of 10,000 or less is adjusted. It is preferable to adjust pH of the fractionated fraction liquid to an acidic side in terms of preventing a carboxyl group of the above mentioned compounds from becoming a salt form. By adjusting the pH to an acidic side, water solubility of the above described compounds becomes smaller, and the compounds can be more reliably extracted in the subsequent organic solvent extraction step. In order to adjust the pH to an acidic side, for example, an inorganic acid such as hydrochloric acid and sulfuric acid or an organic acid such as acetic acid and citric acid may be added to the fraction liquid. Specifically, for example, the pH can be adjusted with an aqueous hydrochloric acid solution. The pH is preferably adjusted to 1 to 4, and more preferably to 1 to 3.

In the organic solvent extraction step, the pH adjusted fraction liquid is extracted with an organic solvent. A general extraction treatment may be used. For example, an extraction treatment using a separatory funnel, an extraction treatment using a Soxhlet extractor, or the like may be used. An extraction temperature is usually 20 to 30° C. An extraction time is, for example, 30 min to 24 hours. An amount of the organic solvent may be, for example, 95% by volume or more. The organic solvent includes, for example, an ester such as ethyl acetate and butyl acetate, a halogenated hydrocarbon such as dichloromethane, chloroform and dichloroethane, an alcohol such as butanol, an ether such as diethyl ether and diisopropyl ether, a ketone such as methyl isobutyl ketone, an aromatic hydrocarbon such as benzene, toluene, xylene and chlorobenzene, and the like.

In the purification step, a general purification treatment method is used. A purification treatment by reverse osmosis, a purification treatment by absorption, or the like may be used.

2. A Coffee Melanoidin

A coffee melanoidin refers to a melanoidin contained in a coffee extract, and includes, for example, compounds having at least an aromatic hydrocarbon structure and a carboxy group in the compounds. The coffee melanoidin is generally said to be a melanoidin produced by Maillard reaction from a saccharide including a polysaccharide, an amino acid including a protein, and a polyphenol including chlorogenic acid. Chlorogenic acid is composed of caffeic acid and quinic acid, and is contained in coffee beans at a concentration of 5 to 10% by mass more than caffeine (at 1 to 2% by mass).

A coffee melanoidin is used in a state of being contained in a coffee extract in the present invention, but it may also be used as a compound isolated and purified from a coffee extract or a compound chemically synthesized. In the case of synthesizing chemically a coffee melanoidin, an amino acid including a protein, a polyphenol including chlorogenic acid, and a saccharide including a polysaccharide, as needed, may be mixed, and then Maillard reaction may be performed by heating, to prepare a coffee melanoidin.

The amino acid may be a natural amino acid or the like. The amino acid includes, for example, glycine, serine, threonine, alanine, arginine, asparagine, aspartic acid, cysteine, glutamine, glutamic acid, histidine, isoleucine, leucine, lysine, methionine, phenylalanine, proline, tryptophan, tyrosine, and valine. The amino acid is preferably glycine, serine, threonine, or the like. A peptide or a protein may also be used as the amino acid.

The saccharide includes, for example, an aldose or ketose having reducibility. The saccharide includes, for example, an aldose such as glucose, galactose, mannose, xylose, erythrose, threose, ribose, arabinose, lyxose and allose, and a ketose such as erythrulose, xylulose, ribulose, psicose, fructose and sorbose. The saccharide is preferably glucose, galactose, mannose, xylose, or the like. An oligosaccharide or a polysaccharide may be used as the saccharide.

A coffee melanoidin can be prepared by mixing and heating the amino acid and chlorogenic acid and, as needed, the saccharide. Specifically, for example, the amino acid and chlorogenic acid (and, as needed, the saccharide) may be dissolved or suspended in a solvent and heated. A mixing molar ratio of the amino acid and chlorogenic acid (and, as needed, the saccharide) includes, for example, 1:2 to 2:1, preferably 1:1.5 to 1.5:1, more preferably 1:1.1 to 1.1:1, particularly preferably 1:1.

The solvent includes, for example, water, an alcohol (e.g., methanol, ethanol, propanol, glycerin, etc.), tetrahydrofuran, dimethyl sulfoxide, N,N-dimethylformamide, acetone, or the like. The solvent is preferably water, an alcohol, and the like, more preferably water. An amount of the solvent may be, for example, 1 to 20 times by mass, preferably 2 to 10 times by mass, more preferably 3 to 6 times by mass with respect to the mass of the mixture of the amino acid and chlorogenic acid (and, as needed, the saccharide). For example, chlorogenic acid (and, as needed, the saccharide) at a concentration of 0.5 to 1.5 M, or preferably 0.8 to 1.2 M, and the amino acid at a concentration of 0.5 to 1.5 M, or preferably 0.8 to 1.2 M, may be added to the solvent and heated.

A pH during the reaction may be, for example, pH 3 to 9, preferably pH 4 to 7.5. As the reaction proceeds, the pH of the reaction system decreases. A molecular weight of a produced coffee melanoidin varies depending on the pH. As the pH is lower, a coffee melanoidin having a higher molecular weight is produced. In order to adjust the pH during the reaction within an appropriate range, a base may also be added. The base to be added includes, for example, an alkali hydroxide such as sodium hydroxide and potassium hydroxide, or an alkali (hydrogen) carbonate such as sodium carbonate, sodium hydrogen carbonate, potassium carbonate and potassium hydrogen carbonate. The base is preferably an alkali (hydrogen) carbonate. An amount of the base may be, for example, 0.05 to 1 mol, preferably 0.07 to 0.3 mol, more preferably 0.9 to 0.15, with respect to 1 mol of the amino acid. On the other hand, an acid such as hydrochloric acid, sulfuric acid, nitric acid, phosphoric acid and methanesulfonic acid may also be added to lower the pH.

A heating temperature may be, for example, 70 to 200° C., preferably 90 to 160° C., more preferably 100 to 130° C. When the heating temperature is higher than the boiling point of the solvent, for example, an autoclave or the like may be used. A heating time may be preferably changed as appropriate according to the heating temperature. The heating time may be, for example, 1 to 10 hours, preferably 2 to 5 hours. After completion of the heating, a coffee melanoidin having a relatively low molecular weight may be isolated by performing extraction, solidification, filtration, drying, purification or the like according to a conventional method.

A coffee melanoidin having a high molecular weight may be obtained by polymerizing the mixture after the above heating under a more acidic condition. The acidic condition may be pH 1 to 4, preferably pH 2 to 3. In order to make the mixture acidic, for example, an acid such as hydrochloric acid, sulfuric acid, phosphoric acid, nitric acid, methanesulfonic acid or the like may be added. The above mixture may be stirred or left under the acidic condition, for example, at 15 to 100° C., preferably at 20 to 60° C., more preferably at 30 to 50° C. for the polymerization. A time for the polymerization may be preferably changed as appropriate according to the warming temperature. The time may be, for example, 1 hour to 1 month, preferably 1 to 7 days, more preferably 2 to 4 days.

After the polymerization, a coffee melanoidin having a high molecular weight may be isolated by performing extraction, solidification, filtration, drying, purification or the like according to a conventional method. As needed, a coffee melanoidin having a certain molecular weight or more, for example, a coffee melanoidin having a molecular weight of 10,000 or more, a coffee melanoidin having a molecular weight of 20,000 or more, and the like may be separated by ultrafiltration. It is preferable to prepare a coffee melanoidin having a desired molecular weight depending on its usage.

3. A Low Temperature Damage Alleviating Agent or a Necrosis Inhibitor, and a Method of Preserving an Organ, a Tissue or Cells of a Living Body The low temperature damage alleviating agent or the necrosis inhibitor of the present invention includes the above coffee extract. The low temperature damage alleviating agent or the necrosis inhibitor of the present invention, for example, alleviates a low temperature damage of an organ, a tissue or cells of a living body, or inhibits necrosis of an organ, a tissue or cells of a living body. Moreover, the low temperature damage alleviating agent or the necrosis inhibitor of the present invention may be used as described below, for example, for preservation of an organ, a tissue or cells of a living body.

The method of preserving an organ, a tissue or cells of a living body of the present invention may be performed by preserving the organ, the tissue or the cells of a living body by using a medium comprising the coffee extract. Any medium may be used as long as the medium can preserve an organ, a tissue or cells of a living body. A concentration of the coffee extract in the medium may be, for example, about 0.001 to 0.5 mg/ml, preferably about 0.005 to 0.1 mg/ml, more preferably about 0.01 to 0.05 mg/ml.

The method of preserving an organ, a tissue or cells of a living body of the present invention is preferably performed at a non-freezing low temperature. A preservation temperature may be, for example, about −10 to 0° C., preferably about −8 to −4° C., more preferably about −7 to −5° C.

In the method for preserving an organ, a tissue or cells of a living body of the present invention, an osmotic pressure regulator such as raffinose and trehalose may be added in addition to the coffee extract. Thereby, a damage of the organ, the tissue or the cells of a living body can be more reduced, and a low temperature damage can be more alleviated, and necrosis can be more inhibited. A concentration of the osmotic pressure regulator in the medium may be, for example, about 0.01 to 5 mM, preferably about 0.05 to 2 mM, more preferably about 0.1 to 1.5 mM.

EXAMPLES

Hereinafter, the present inventions are further explained in detail by Examples. However, the present inventions are not limited to these at all.

Example 1

Preparation of a Coffee Extract

Beans of a plant (Coffea arabica) belonging to Coffea were roasted at 180° C. 100 g of the roasted coffee beans were added to 500 mL of deionized water, and extracted at 90° C. for 1 hour in an autoclave, and the residue after extraction was removed by centrifugation (8,000 g, 20 mM). Subsequently, a fraction liquid having a molecular weight of 10,000 or less was obtained by ultrafiltration of the obtained water extract by using an ultrafiltration apparatus (Nippon Millipore Corporation, Amicon Stirred Cells Model 18400) equipped with an ultrafiltration membrane with a molecular weight cut off of 10,000 (Nippon Millipore Corporation, Ultrafiltration disk, Ultracell, PL, regenerated cellulose, 10,000 NMWL). pH was adjusted to 2.0 by adding an aqueous hydrochloric acid solution to the fraction liquid after fractionation. The obtained fraction liquid and ethyl acetate were added in a separatory funnel, and the separatory funnel was shaken to perform an organic solvent extraction step. Then, the ethyl acetate layer was taken out, and ethyl acetate was evaporated to obtain a solid coffee extract (yield 1.7%).

Example 2

Preparation of a Coffee Melanoidin 100 mL of a distilled water solution in which chlorogenic acid and glutamic acid were dissolved at each concentration of 1 M, was prepared. To the solution, was further added sodium hydrogen carbonate so that the concentration was 0.1 M, and was dissolved. pH of the solution after addition of sodium hydrogen carbonate was adjusted to 7.0 with 1 M aqueous sodium hydroxide solution. Then, the solution was heated at 120° C. for 120 min in an autoclave. pH of the heated solution was adjusted to 2.0 with 1 M hydrochloric acid, and the solution was fractionated with twice volume of ethyl acetate. The obtained ethyl acetate layer was evaporated and dried with an evaporator to obtain a coffee melanoidin.

Example 3

Preparation of a Sample Liquid of the Coffee Extract and the Coffee Melanoidin

Ultrapure water was added to the coffee extract obtained in Example 1 and the coffee melanoidin obtained in Example 2, so that each concentration was 0.048 mg/mL, to prepare a sample liquid.

Test Example 1

Cell Viability Test in a Non-Freezing State

FBS (Thermo Fisher Scientific Co., Ltd.) was added to Ham's F12 medium (Thermo Fisher Scientific Co., Ltd.) so that the concentration of FBS in Ham F12 medium was 10%. CHO-K1 cells (ATCC) was added and suspended at $3.0 \times 10^5$ cells/mL in the Ham's F12 medium after addition of FBS, to prepare a cell suspension. 125 μL of the obtained cell suspension was seeded in a 96-well plate and cultured at 37° C. under 5% $CO_2$ for 24 hours. 10 μL of ultrapure water (control), the sample liquid of the coffee extract or the sample liquid of the coffee melanoidin was added to each well, and stored at 0° C. for 10 min, and then cooled down at −0.1° C./min, and stored in a non-freezing state at −6.5° C. for 7 to 8 days. The number of viable cells was measured by color development using the water-soluble tetrazolium salt WST-8 at the start of storage (day 0), 2 days, 4 days, 6 days, and 8 days after storage. Cell viability (%) was calculated based on the number of viable cells at the start of storage.

Table 1 and FIG. 1 show the test results of the sample liquid of the coffee extract prepared in Example 3 and ultrapure water (control). As shown below, most of the cells without addition of the coffee extract died of necrosis by low temperature damage in a non-freezing state at −6.5° C. during 4 days. On the other hand, low temperature damage was reduced, and necrosis was inhibited by addition of the coffee extract.

TABLE 1

| | Cell viability (%) | |
| --- | --- | --- |
| Storage days (day) | Coffee extract added | No additives |
| 0 | 100 | 100 |
| 2 | 111 | 103 |
| 4 | 111 | 7.24 |
| 6 | 12.8 | 7.09 |

Figure 2:
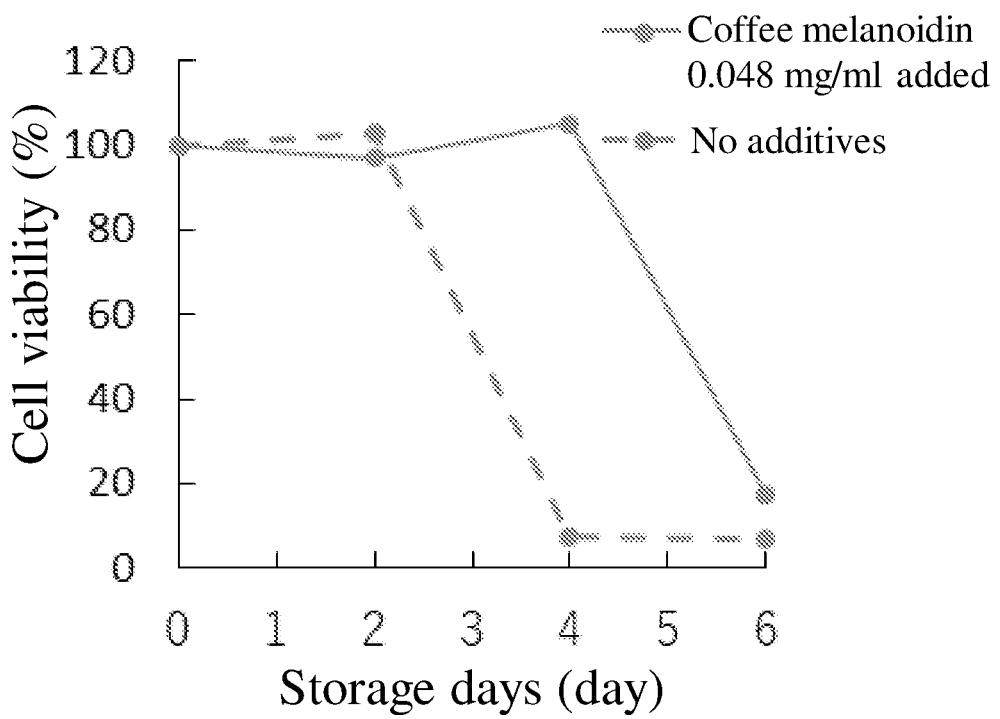
FIG. 2 shows a figure exhibiting the test result of the coffee melanoidin in Example 2.

Table 2 and FIG. 2 show the test results of the sample liquid of the coffee melanoidin prepared in Example 3 and ultrapure water (control). As shown below, most of the cells without addition of the coffee melanoidin died of necrosis by low temperature damage in a non-freezing state at −6.5° C. during 4 days. On the other hand, low temperature damage was reduced, and necrosis was inhibited by addition of the coffee melanoidin.

TABLE 2

| | Cell viability (%) | |
| --- | --- | --- |
| Storage days (day) | Coffee melanoidin added | No additives |
| 0 | 100 | 100 |
| 2 | 97 | 103 |

TABLE 2-continued

| | Cell viability (%) | |
|---|---|---|
| Storage days (day) | Coffee melanoidin added | No additives |
| 4 | 105 | 7.24 |
| 6 | 17.1 | 7.09 |

As described above, the coffee extract has an excellent low temperature alleviating damage effect and an excellent necrosis inhibiting effect. Therefore, an organ, a tissue or cells of a living body can be preserved without damaging the organ, the tissue or the cells by using a medium comprising a coffee extract.

INDUSTRIAL APPLICABILITY

The present inventions provide a method of preserving an organ, a tissue or cells of a living body at a non-freezing low temperature stably without damaging the organ, the tissue or the cells, and provide a low temperature damage alleviating agent or a necrosis inhibitor capable of being used for the method or the like.

The invention claimed is:

1. A method of preserving an isolated organ, an isolated tissue or isolated cells, comprising preserving the isolated organ, the isolated tissue, or the isolated cells in a medium comprising coffee melanoidin at a concentration of about 0.001 to 0.5 mg/ml at a temperature of about −10 to 0° C. for up to 6 days.

2. The method according to claim 1, wherein the isolated organ, the isolated tissue or the isolated cells is preserved at a low temperature of about −8 to −4° C.

3. The method according to claim 1, wherein ATP depletion of the isolated organ, the isolated tissue or the isolated cells during preservation is delayed.

4. The method of claim 1, wherein the coffee melanoidin is a melanoidin having a molecular weight of 10,000 or more.

5. The method of claim 1, wherein the coffee melanoidin is the melanoidin obtained by mixing an aqueous coffee extract with an organic solvent to perform an organic solvent extraction step that provides an organic fraction and obtaining the coffee melanoidin from the organic fraction.

6. The method according to claim 1, comprising a step of preserving the isolated organ, the isolated tissue or the isolated cells in a medium comprising coffee melanoidin at a temperature of about −10 to 0° C. for 0 to 4 days.

7. The method according to claim 1, wherein the coffee melanoidin is a compound chemically synthesized melanoidin.

* * * * *